United States Patent [19]

Chu et al.

[11] Patent Number: 5,334,795
[45] Date of Patent: * Aug. 2, 1994

[54] PRODUCTION OF ETHYLBENZENE

[75] Inventors: Pochen Chu, Voorhees; Michael E. Landis, Woodbury; Quang N. Le, Cherry Hill, all of N.J.

[73] Assignee: Mobil Oil Corp., Fairfax, Va.

[*] Notice: The portion of the term of this patent subsequent to Oct. 9, 2007 has been disclaimed.

[21] Appl. No.: 967,954

[22] Filed: Oct. 27, 1992

Related U.S. Application Data

[63] Continuation of Ser. No. 786,617, Nov. 1, 1991, abandoned, which is a continuation-in-part of Ser. No. 545,163, Jun. 28, 1990, abandoned.

[51] Int. Cl.$^5$ ............................................. C07C 2/66
[52] U.S. Cl. ................................. 585/467; 585/446; 585/453
[58] Field of Search .................................... 585/467

[56] References Cited

U.S. PATENT DOCUMENTS

| | | | |
|---|---|---|---|
| 2,904,607 | 9/1959 | Mattox et al. | 260/671 |
| 3,251,897 | 5/1966 | Wise | 260/671 |
| 3,631,120 | 12/1971 | Eberly et al. | 260/671 |
| 3,641,177 | 2/1972 | Eberly et al. | 260/671 |
| 3,751,504 | 8/1973 | Keown et al. | 260/672 |
| 3,751,506 | 8/1973 | Burress | 260/671 |
| 3,755,483 | 8/1973 | Burress | 260/671 |
| 3,917,734 | 11/1975 | de Rosset | 585/828 |
| 4,016,218 | 4/1977 | Haag et al. | 260/671 |
| 4,169,111 | 9/1979 | Wight | 585/323 |
| 4,301,316 | 11/1981 | Young | 585/455 |
| 4,301,317 | 11/1981 | Young | 585/455 |
| 4,393,262 | 7/1983 | Kaeding | 585/467 |
| 4,421,941 | 12/1983 | Olson et al. | 585/475 |
| 4,439,409 | 3/1984 | Pappe et al. | 423/328 |
| 4,459,426 | 7/1984 | Inwood et al. | 585/323 |
| 4,469,908 | 9/1984 | Burress | 585/467 |
| 4,547,605 | 11/1985 | Kresge et al. | 585/467 |
| 4,826,667 | 5/1989 | Zones et al. | 423/277 |
| 4,891,458 | 1/1990 | Innes et al. | 585/323 |
| 4,954,325 | 9/1990 | Rubin et al. | 423/328 |
| 4,962,256 | 10/1990 | Le et al. | 585/467 |
| 4,992,606 | 2/1991 | Kushnerick et al. | 585/467 |
| 5,073,653 | 12/1991 | Butler | 585/467 |
| 5,077,445 | 12/1991 | Le | 585/467 |
| 5,118,894 | 6/1992 | Le | 585/467 |
| 5,149,894 | 9/1992 | Holtermann et al. | 585/467 |

FOREIGN PATENT DOCUMENTS

| | | |
|---|---|---|
| 231860 | 1/1986 | European Pat. Off. |
| 293032 | 5/1987 | European Pat. Off. |

*Primary Examiner*—Anthony McFarlane
*Attorney, Agent, or Firm*—Alexander J. McKillop; Dennis P. Santini; Edward F. Kenehan, Jr.

[57] ABSTRACT

Ethylbenzene is produced by the alkylation of benzene with ethylene in the presence of an alkylation catalyst having a particular structure defined by its X-ray diffraction pattern. A preferred catalyst is the zeolite MCM-22. The process is typically carried out at a temperature of 300° to 1000° F. but the catalyst provides sufficient activity for the reaction to be carried out at temperatures below 700° F. Liquid phase operation is preferred, giving a lower yield of polyethylated products. The use of the selected catalyst also results in a reduction of the xylene impurity level to values below 500 ppm in the product.

11 Claims, No Drawings

PRODUCTION OF ETHYLBENZENE

CROSS-REFERENCE TO RELATED APPLICATIONS

This application is a continuation of U.S. application Ser. No. 07/786,617, filed Nov. 1, 1991, now abandoned, which is a continuation-in-part of U.S. application Ser. No. 07/545,163, filed Jun. 28, 1990, now abandoned.

This application is also related to U.S. application Ser. No. 07/469,998, filed Jan. 25, 1990, now U.S. Pat. No. 4,992,606.

FIELD OF THE INVENTION

This invention relates to an improved process for the production of ethylbenzene.

BACKGROUND OF THE INVENTION

Ethylbenzene is a valuable commodity chemical which is currently used on a large scale industrially for the production of styrene monomer. Ethylbenzene may be produced by a number of different chemical processes but one process which has achieved a significant degree of commercial success is the alkylation of benzene with ethylene in the presence of a solid, acidic zeolite catalyst. In the production of ethylbenzene by this process, ethylene is used as the alkylating agent and is reacted with benzene in the presence of the catalyst at temperatures which vary between the critical temperature of benzene up to 900° F. (about 480° C.) at the reactor inlet. The reactor bed temperature may be as much as 150° F. (about 85° C.) above the reactor inlet temperature and typical temperatures for the benzene/ethylene reaction vary from 600° to 900° F. (315° to 480° C.), but are usually maintained above about 700° F. (about 370° C.) in order to keep the content of the more highly alkylated benzenes such as diethyl benzene at an acceptably low level. Pressures typically vary from atmospheric to 3000 psig (about 20785 kPa abs) with a molar ratio of benzene to ethylene from about 1:1 to 25:1, usually about 5:1 (benzene:ethylene). Space velocity in the reaction is high, usually in the range of 1 to 6, typically 2 to 5, WHSV based on the ethylene flow, with the benzene space velocity varying accordingly, in proportion to the ratio of the reactants. The products of the reaction include ethylbenzene which is obtained in increasing proportions as temperature increases together with various polyethylbenzenes, principally diethyl benzene (DIEB) which also are produced in increasing amounts as reaction temperature increases. Under favorable operating conditions on the industrial scale, an ethylene conversion in excess of 99.8 weight percent may be obtained at the start of the cycle In the commercial operation of this process, the polyalkylated benzenes, including both polymethylated and polyethylated benzenes are recycled to the alkylation reactor in which the reaction between the benzene and the ethylene takes place. By recycling the by-products to the alkylation reaction, increased conversion is obtained as the polyethylated benzenes (PEB) are converted to ethylbenzene (EB). In addition, the presence of the PEB during the alkylation reaction reduces formation of these species through equilibration of the components because at a given feed composition and under specific operating conditions, the PEB recycle will reach equilibrium at a certain level.

Ethylbenzene production processes are described in U.S. Pat. Nos. 3,751,504 (Keown), 4,547,605 (Kresge) and 4,016,218 (Haag); reference is made to these patents for a detailed description of such processes. The process described in U.S. Pat. No. 3,751,504 is of particular note since it includes a separate transalkylation step in the recycle loop which is effective for converting a significant proportion of the more highly alkylated products to the desired ethylbenzene product. Other processes for the production of ethylbenzene are disclosed in U.S. Pat. Nos. 4,169,11 (Wight) and 4,459,426 (Inwood), in both of which a preference for large pore size zeolites such as zeolite Y is expressed, in distinction to the intermediate pore size zeolites used in the processes described in the Keown, Kresge and Haag patents. U.S. Pat. No. 3,755,483 (Burress) describes a process for the production of ethylbenzene using zeolite ZSM-12 as the alkylation catalyst.

SUMMARY OF THE INVENTION

We have now found that the certain crystalline catalytic materials having a crystalline structure defined by a characteristic X-ray diffraction pattern are extremely effective catalysts for the production of ethylbenzene.

According to the present invention, therefore, we provide a process for the production of ethylbenzene by the ethylation of benzene in the presence of an alkylation catalyst which comprises a synthetic porous crystalline material characterized by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms.

A preferred catalyst of this type includes the synthetic zeolite identified in this specification as MCM-22.

The process can be carried out at high ethylene conversion to produce an ethylbenzene product with very low content of impurities such as xylenes, cumene, butylbenzene and heavy aromatic residues including the more highly alkylated benzenes. The xylene level of the product is notably low at less than about 500 ppm, which is an important advantage commercially. The catalyst is highly resistant to aging and is notable for having enhanced activity at relatively low temperatures, enabling the alkylation reaction to be carried out at lower temperatures at which smaller proportions of impurities, especially xylenes, are produced without, however, significantly increasing the proportion of diethylbenzene in the product. The MCM-22 catalyst is also highly resistant to aging and is therefore capable of maintaining an extended cycle life between successive reactivation treatments.

DETAILED DESCRIPTION

Alkylation Catalyst

In the production of ethylbenzene, benzene is alkylated with ethylene in the presence of a solid, porous acidic catalytic material which a characteristic X-ray diffraction pattern. In its calcined form, the synthetic porous crystalline material component employed in the catalyst is characterized by an X-ray diffraction pattern including the lines shown in Table 1 below:

TABLE 1

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.18 ± 0.12 | M-VS |

TABLE 1-continued

| Interplanar d-Spacing (A) | Relative Intensity, $I/I_o \times 100$ |
|---|---|
| 6.00 ± 0.10 | W-M |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines shown in Table 2 below:

TABLE 2

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines shown in Table 3 below:

TABLE 3

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, it may be characterized in its calcined form by an X-ray diffraction pattern including the following lines shown in Table 4 below:

TABLE 4

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |

TABLE 4-continued

| Interplanar d-Spacing (A) | Relative Intensity, $I/I_o \times 100$ |
|---|---|
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstrom Units (Å), corresponding tot he recorded lines, were determined. In Tables 1–4, the relative intensities are given in terms of the symbols W=weak, M=medium, S=strong, VS=very strong. In terms of intensities, these may be generally designated as follows:

| W = | 0–20 |
| M = | 20–40 |
| S = | 40–60 |
| VS = | 60–100 |

These X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Examples of such porous crystalline materials include the PSH-3 composition of U.S. Pat. No. 4,439,409, to which reference is made for a description of this material as well as of its preparation. Another crystalline material of this type is the synthetic zeolite MCM-22.

Zeolite MCM-22 has a chemical composition expressed by the molar relationship:

$$X_2O_3:(n)YO_2,$$

where X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

where R is an organic component. The Na and R components are associated with the zeolite as a result of their presence during crystallization, and are easily removed by the post-crystallization methods described below.

Zeolite MCM-22 is thermally stable and exhibits a high surface area greater than about 400 m$^2$/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the alkylation catalyst composition herein without having to first undergo an exchange step. To the extent desired, however, the original sodium cations of the as-synthesized material can be replaced at least in part by established techniques including ion exchange with other cations. Preferred replacement cations include metal ions, hydrogen ions, hydrogen precursor ions, e.g., ammonium and mixtures of such ions.

In its calcined form, zeolite MCM-22 appears to be made up of a single crystal phase with little or no detectable impurity crystal phases and has an X-ray diffraction pattern including the lines listed in above Tables 1–4.

Prior to its use as alkylation catalyst, the zeolite crystals should be subjected to thermal treatment to remove part or all of any organic constituent present in the as-synthesised material.

The zeolite in its as-synthesised form containing organic cations as well as when it is in its ammonium form, can be converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to a limit imposed by the irreversible thermal degradation of the crystalline structure of the zeolite, typically up to about 925° C.

Prior to its use in the alkylation process, the zeolite crystals should be dehydrated, at least partially. This can be done by heating the crystals to a temperature in the range of from about 200° C. to about 595° C. in an atmosphere such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prepared from a reaction mixture containing sources of alkali or alkaline earth metal (M), e.g., sodium or potassium, cation, an oxide of trivalent element X, e.g, aluminum, an oxide of tetravalent element Y, e.g., silicon, an organic (R) directing agent, described below, and water. The reaction mixture has a composition, in terms of mole ratios of oxides, within the following ranges:

| Reactants | Useful | Preferred |
|---|---|---|
| YO$_2$/X$_2$O$_3$ | 10–60 | 10–40 |
| H$_2$O/YO$_2$ | 5–100 | 10–50 |
| OH$^-$/YO$_2$ | 0.01–1.0 | 0.1–0.5 |
| M/YO$_2$ | 0.01–2.0 | 0.1–1.0 |
| R/YO$_2$ | 0.05–1.0 | 0.1–0.5 |

The organic directing agent for use in synthesizing zeolite MCM-22 from the above reaction mixture is hexamethyleneimine.

In a preferred method of synthesizing zeolite MCM-22, the YO$_2$ reactant contains a substantial amount of solid YO$_2$, e.g., at least about 30 wt. % solid YO$_2$. Where YO$_2$ is silica, the use of a silica source containing at least about 30 wt. % solid silica, e.g., Ultrasil (a precipitated, spray dried silica containing about 90 wt. % silica) or HiSil (a precipitated hydrated SiO$_2$ containing about 87 wt. % silica, about 6 wt. % free H$_2$O and about 4.5 wt. % bound H$_2$O of hydration) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt. % of SiO$_2$, 8.9 wt. % Na$_2$O and 62.3 wt. % H$_2$O) is used, crystallization may yield little if any MCM-22 crystalline material and impurity phases of other crystal structures, e.g., ZSM-12, may be produced. Preferably, therefore, the YO$_2$, e.g., silica, source contains at least about 30 wt. % solid YO$_2$, e.g., silica, and more preferably at least about 40 wt. % solid YO$_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days, after which the crystals are separated from the liquid and recovered.

The reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals (based on total weight) of the crystalline product.

The zeolite crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The crystalline material may be composited with another material which is resistant to the temperatures and other conditions employed in the alkylation process of this invention. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the zeolite, i.e., combined therewith or present during its synthesis, which itself is catalytically active may change the conversion and/or selectivity of the catalyst. Inactive materials suitably serve diluents to control the amount of conversion so that alkylation products can be obtained economically and orderly without employing other means controlling the rate of reaction. These materials may be incorporated into naturally occurring clays, e.g., bentonite and kaolin, to improve the crush strength of the catalyst under commercial alkylation operating conditions and function as binders or matrices for the catalyst. The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the catalyst used in the present process may be increased by steaming. U.S. Pat. Nos. 4,663,492; 4,594,146; 4,522,929; and 4,429,176, describe conditions for the steam stabilization of zeolite catalysts which can be utilized to steam-stabilize the catalyst. Reference is made to these patents for a detailed description of the steam stabilization technique for use with the present catalysts. The steam stabilization conditions typically include contacting the catalyst with, e.g., 5–100% steam at a temperature of at least about 300° C. (e.g., 300°–650° C.) for at least one hour (e.g., 1–200 hours) at a pressure of 101–2,500 kPa. In a more particular embodiment, the catalyst can be made to undergo steaming with 75–100% steam at 315°–500° C. and atmospheric pressure for 2–25 hours. The steaming of the catalyst can take place under conditions sufficient to initially increase the Alpha Value of the catalyst, the significance of which is discussed below, and produce a steamed catalyst having an enhanced Alpha Value. If desired, steaming can be continued to subsequently reduce the Alpha Value from the higher Alpha Value to an Alpha Value which is substantially the same as the Alpha Value of the unsteamed catalyst.

The preparation of various MCM-22 catalytic materials is described in detail in Examples 9 to 16 below. In these Examples illustrating the synthesis of zeolite, sorption data for water, cyclohexane and/or n-hexane adsorption were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22 and are preferred for the zeolite component of catalyst for use herein.

The alkylation reaction between the benzene and the ethylene requires a the alkylation catalyst to possess acidic activity and for this reason the catalyst will normally have a relatively high alpha value. Alpha values of at least about 10 e.g. 40 or higher are typical, and values above 100 have been demonstrated as useful in this process. A zeolite alpha value is an approximate indication of the catalytic cracking (acidic) activity of the catalyst compared to a standard catalyst and it gives a relative rate constant based on the activity of a highly active silica-alumina cracking catalyst taken as an Alpha of 1 (Rate Constant=0.016 sec$^{-1}$). The Alpha Test is described in U.S. Pat. No. 3,354,078, in the *Journal of Catalysts,* Vol. 4, p. 527 (1965); Vol. 6, p. 278 (1966); and Vol. 61, p. 395 (1980), to which reference is made for that description. The experimental conditions of the tests reported here include a constant temperature of 538° C. and a variable flow rate as described in detail in the *Journal of Catalysis,* Vol. 61, p. 395. Excessive activity may lead to the production of undesired quantities of xylenes by secondary reactions and for this reason, alpha values of 10 to 100 will normally be adequate although higher alpha values, e.g. 100 to 500, may be employed.

Alkylation Reaction

The alkylation reaction is typically carried out at elevated temperatures either in the liquid or the vapor phase. In the liquid phase, the reaction is carried out with the benzene feedstock in the liquid phase with the reaction conditions (temperature, pressure) appropriate to this end. Suitable conditions can be selected by reference to the phase diagram for benzene. In the vapor phase reaction, the conditions are selected to maintain the benzene in the vapor phase, for example, with a reactor inlet temperature which is above the temperature required to maintain the benzene in the vapor phase at the selected pressure, with a preferred maximum of about 900° F. (about 480° C.). Because the reaction is exothermic, the reactor bed temperature will be higher than the reactor inlet temperatures, typically by as much as about 150° F. (about 85° C.) but generally it is preferred to control the exotherm to a maximum of about 100° F. (55° C.). In most cases, the reaction temperature will be from about 300° F. (about 150° C.) to about 850° F. (about 455° C.) with the yield of ethylbenzene increasing with increasing temperatures. Normally, a temperature of at least 500° F. (about 260° C.) will be used in when the process is operated in the vapor phase mode. Liquid phase operation is normally carried out at temperatures between 300° and 500° F. (about 150° to 260° C.), usually in the range of 400° to 500° F. (about 205° to 260° C.). Because the yield of PEB and certain other by-products usually decreases with increasing temperature, higher temperatures toward 900° F. (about 480° C.) would bE preferred, although a disadvantage of these higher temperatures is that the yield of xylenes would be increased. The advantage of the MCM-22 catalyst is that it is relatively more active at lower temperatures than other zeolite catalysts so that lower temperatures can be used, with a consequent decrease in the proportion of the level of xylene impurities in the product, enabling the xylene contant to be kept below 500 ppmw. Although this would normally be expected to result in an increase in the level of other impurities, especially diethylbenzene and higher alkylation products, it has been found that the use of the lower temperatures with this catalyst does not result in any significant increase in the levels of these products, so that an ethylbenzene product with a significantly lower level of all impurities, including xylenes and ethylbenzene, is obtained.

Pressures during the alkylation step typically are between atmospheric and about 3000 psig, (about 20875 kPa abs.) and generally will not exceed 1000 psig (about 7000 kPa). Relatively low temperature atmospheric pressures, for example, about 50 or 100 psig (about 445 or 790 kPa abs), sufficient to maintain the desired flow rates through the reaction bed will normally be satisfactory. The reaction is carried out in the absence of hydrogen and accordingly the prevailing pressures are those of the reactant species. The reaction may be carried out in the liquid or vapor phases. In a typical low pressure vapor phase operation, the temperature will be from about 600° to 800° F. with the pressure from about 50 to 500 psig, usually 200 to 500 psig. In a typical high pressure liquid phase operation, the temperature will be from about 300° to 600° F. with the pressure in the range of about 400 to 800 psig. The space velocity is from about 0.1 to 10 WHSV, based on the ethylene feed, but is usually maintained at a relatively high value e.g. 1 to 10 WHSV, typically between 1 to 6 WHSV, based on the ethylene, for the gas phase reaction although lower space velocities are appropriate for the liquid phase reaction, for example, from about 0.1 to about 1WHSV with values from about 0.2 to 0.5 WHSV (ethylene) being typical. The ratio of the benzene to the ethylene in the alkylation reactor is typically from 1:1 to 30:1 molar (benzene:ethylene, fresh feed) normally about 5:1 to 20:1 and in most cases from about 5:1 to 10:1 molar, based on the fresh feed, although the ratio in the reactors may be higher as a result of the benzene recycle, with ratios above 30:1 being common, typically about 30:1 to 50:1.

The use of temperatures significantly above about 950° F. is undesirable because at these high temperatures, a number of undesirable reactions occur. The reactants and the alkylated products undergo degradation resulting in the loss of the desired products as well as the reactants and in addition, undesirable residues may be formed from other side reactions. The ethylene which functions as the alkylating agent will tend to polymerize with itself, especially at high pressures or with other reactants to form resinous compounds within the reaction zone. These resinous compounds together with the degradation products may lead to the formation of coke-like deposits on the active surfaces of the catalyst which will rapidly inhibit the high activity necessary in the catalyst for acceptable conversion rates. The use of temperatures below about 900° F. (about 480° C.) will normally enable these problems to be maintained within acceptable bounds.

The alkylation process can be carried out as a batch-type, semi-continuous or continuous operation utilizing a fixed, fluidized or moving bed catalyst system. The process is, however, preferably operated in the general manner described in U.S. Pat. No. 3,751,504 (Keown) but using MCM-22 as the alkylation catalyst. Reference is made to U.S. Pat. No. 3,751,504 for a description of the process configuration. The use of the separate transalkylation reactor in the recycle loop for the higher alkylated products is desirable for the reasons set out in the Keown patent. The transalkylation catalyst may be an acidic zeolite such as an intermediate pore size zeolite e.g. ZSM-5, as discussed in the Keown patent or, alternatively, may be also MCM-22 itself. Because any propyl benzene in the recycle stream has a particular tendency to react with ethylene to form the high boiling aromatic residues which tend to degrade catalyst activity relatively rapidly, its effective removal in the transalkylation/dealkylation reactor results in an increase in cycle life.

Examples 1 to 8, immediately following, illustrate the preparation of MCM-22 catalyst.

EXAMPLE 1

One part of sodium aluminate (43.5% Al2O3, 32.2% Na2O, 25.6% H2O) was dissolved in a solution containing 1 part of 50% NaOH solution and 103.13 parts H2O. To this was added 4.50 parts hexamethyleneimine. The resulting solution was added to 8.55 parts of Ultrasil, a precipitated, spray-dried silica (about 90% SiO2).

The reaction mixture had the following composition, in mole ratios:

| | |
|---|---|
| $SiO_2/Al_2O_3 =$ | 30.0 |
| $OH^-/SiO_2 =$ | 0.18 |
| $H_2O/SiO_2 =$ | 44.9 |
| $Na/SiO_2 =$ | 0.18 |
| $R/SiO_2 =$ | 0.35 | where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table 5 below.

TABLE 5

| Degrees 2-Theta | Interplanar d-Spacing (A) | $I/I_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |

TABLE 5-continued

| Degrees 2-Theta | Interplanar d-Spacing (A) | I/I$_o$ |
|---|---|---|
| 34.61 | 2.592 | 5 |

The sorption capacities of the calcined material were measured to be:

| | |
|---|---|
| H$_2$O | 15.2 wt. % |
| Cyclohexane | 14.6 wt. % |
| n-Hexane | 16.7 wt. % |

The surface area of the calcined crystalline material was measured to be 494 m$^2$/g.

The chemical composition of the uncalcined material was determined to be as follows:

| Component | Wt. % |
|---|---|
| SiO$_2$ | 66.9 |
| Al$_2$O$_3$ | 5.40 |
| Na | 0.03 |
| N | 2.27 |
| Ash | 76.3 |
| SiO$_2$/Al$_2$O$_3$, mole ratio | 21.1 |

A portion of the calcined crystalline product was tested in the Alpha Test and was found to have an Alpha Value of 224.

EXAMPLES 2–4

Three separate synthesis reaction mixtures were prepared with compositions indicated in Table 6 below. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table 6. The sorption and surface area measurements were of the calcined product.

TABLE 6

| Example | 2 | 3 | 4 |
|---|---|---|---|
| Synthesis Mixture, mole ratios | | | |
| SiO$_2$/Al$_2$O$_3$ | 30.0 | 30.0 | 30.0 |
| OH$^-$/SiO$_2$ | 0.18 | 0.18 | 0.18 |
| H$_2$O/SiO$_2$ | 19.4 | 19.4 | 44.9 |
| Na/SiO$_2$ | 0.18 | 0.18 | 0.18 |
| R/SiO$_2$ | 0.35 | 0.35 | 0.35 |
| Product Composition, Wt. % | | | |
| SiO$_2$ | 64.3 | 68.5 | 74.5 |
| Al$_2$O$_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| SiO$_2$/Al$_2$O$_3$, molar | 22.5 | 20.9 | 26.0 |
| Adsorption, Wt. % | | | |
| H$_2$O | 14.9 | 13.6 | 14.6 |
| Cyclohexane | 12.5 | 12.2 | 13.6 |
| n-Hexane | 14.6 | 16.2 | 19.0 |
| Surface Area, m$^2$/g | 481 | 492 | 487 |

Quantities of the calcined (538° C. for 3 hours) crystalline silicate products of Examples 10, 11 and 12 were tested in the Alpha Test and found to have Alpha Values of 227, 180 and 187, respectively.

EXAMPLE 5

To demonstrate a further preparation of the zeolite MCM-22, 4.49 parts of hexamethyleneimine was added to a solution containing 1 part of sodium aluminate, 1 part of 50% NaOH solution and 44.19 parts of H$_2$O. To the combined solution were added 8.54 parts of Ultrasil silica. The mixture was crystallized with agitation at 145° C. for 59 hours and the resultant product was water washed and dried at 120° C.

Product chemical composition, surface area and adsorption analyses results were as set forth in Table 7. The surface area and sorption analyses were performed on the calcined sample, the chemical composition on the uncalcined material.

TABLE 7

| Product Composition | |
|---|---|
| C | 12.1 wt. % |
| N | 1.98 wt. % |
| Na | 640 ppm |
| Al$_2$O$_3$ | 5.0 wt. % |
| SiO$_2$ | 74.9 wt. % |
| SiO$_2$/Al$_2$O$_3$, mole ratio | 25.4 |
| Adsorption, wt. % | |
| Cyclohexane | 9.1 |
| N-Hexane | 14.9 |
| H$_2$O | 16.8 |
| Surface Area, m$^2$/g | 479 |

EXAMPLE 6

Twenty-five grams of solid crystal product of Example 14 were calcined in a flowing nitrogen atmospheres at 538° C. for 5 hours, followed by purging with 5% oxygen gas (balance N$_2$) for another 16 hours at 538° C.

Individual 3 g samples of the calcined material were ion-exchanged with 100 ml of 0.1N TEABr, TPABr and LaCl$_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Exchange Ions | TEA | TPA | La |
|---|---|---|---|
| Ionic Composition, wt. % | | | |
| Na | 0.095 | 0.089 | 0.063 |
| N | 0.30 | 0.38 | 0.03 |
| C | 2.89 | 3.63 | — |
| La | — | — | 1.04 |

The La-exchanged sample was sized to 14 to 25 mesh and then calcined in air at 538° C. for 3 hours. The calcined material had an Alpha Value of 173.

The calcined sample of the La-exchanged material was severely steamed at 649° C. in 100% steam for 2 hours. The steamed sample had an Alpha Value of 22, demonstrating that the zeolite has very good stability under severe hydrothermal treatment.

EXAMPLE 7

This example illustrates the preparation of the zeolite MCM-22 where X in the general formula above is boron. Boric acid, 2.59 parts, was added to a solution containing 1 part of 45% KOH solution and 42.96 parts H$_2$O. To this was added 8.56 parts of Ultrasil silica, and the mixture was thoroughly homogenized. A 3.88 parts quantity of hexamethyleneimine was added to the mixture.

| | |
|---|---|
| SiO$_2$/B$_2$O$_3$ = | 6.1 |
| OH$^-$/SiO$_2$ = | 0.06 |
| H$_2$O/SiO$_2$ = | 19.0 |
| K/SiO$_2$ = | 0.06 |
| R/SiO$_2$ = | 0.30 | where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

| | |
|---|---|
| H$_2$O (12 Torr) | 11.7 wt. % |
| Cyclohexane (40 Torr) | 7.5 wt. % |
| n-Hexane (40 Torr) | 11.4 wt. % |

The surface area of the calcined crystalline material was measured (BET) to be 405 m$^2$/g.

The chemical composition of the uncalcined material was determined to be as follows:

| | |
|---|---|
| N | 1.94 wt. % |
| Na | 175 ppm |
| K | 0.60 wt. % |
| Boron | 1.04 wt. % |
| Al$_2$O$_3$ | 920 ppm |
| SiO$_2$ | 75.9 wt. % |
| Ash | 74.11 wt. % |
| SiO$_2$/Al$_2$O$_3$, molar ratio | 1406 |
| SiO$_2$/(Al + B)$_2$O$_3$, molar ratio | 25.8 |

A portion of the calcined crystalline product of was treated with NH$_4$Cl and again calcined. The final crystalline product was tested in the Alpha Test and found to have an Alpha Value of 1.

EXAMPLE 8

This example illustrates another preparation of the zeolite in which X of the general formula above is boron. Boric acid, 2.23 parts, was added to a solution of 1 part of 50% NaOH solution and 73.89 parts H$_2$O. To this solution was added 15.29 parts of HiSil silica followed by 6.69 parts of hexamethyleneimine. The reaction mixture had the following composition in mole ratios:

| | |
|---|---|
| SiO$_2$/B$_2$O$_3$ | 12.3 |
| OH$^-$/SiO$_2$ | 0.056 |
| H$_2$O/SiO$_2$ | 18.6 |
| K/SiO$_2$ | 0.056 |
| R/SiO$_2$ | 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| H$_2$O (12 Torr) | 14.4 wt. % |
| Cyclohexane (40 Torr) | 4.6 wt. % |
| n-Hexane (40 Torr) | 14.0 wt. % |

The surface area of the calcined crystalline material was measured to be 438 m$^2$/g.

The chemical composition of the uncalcined material was determined to be as follows:

| Component | Wt. % |
|---|---|
| N | 2.48 |
| Na | 0.06 |
| Boron | 0.83 |
| Al$_2$O$_3$ | 0.50 |
| SiO$_2$ | 73.4 |
| SiO$_2$/Al$_2$O$_3$, molar ratio | 249 |
| SiO$_2$/(Al + B)$_2$O$_3$, molar ratio | 28.2 |

A portion of the calcined crystalline product was tested in the Alpha Test and found to have an Alpha Value of 5.

EXAMPLE 9

This Example illustrates the use of the MCM-22 catalyst in the preparation of ethylbenzene. The MCM-22 base material used was an unsteamed sample of MCM-22 having an alpha value of 270. For comparison purposes, ZSM-5 alkylation catalysts were also used. The following catalysts were prepared:

Catalyst 1.—an unbound MCM-22 acid form zeolite from MCM-22 base.

Catalyst 2.—an alumina bound extrudate of MCM-22 (65% MCM-22, 35% Al$_2$O$_3$), same MCM-22 base as Catalyst 1.

Catalyst 3.—a steamed alumina bound ZSM-5 extrudate.

Catalyst 4.—a fresh alumina bound ZSM-5 extrudate.

The four catalysts were tested in a low pressure, vapor phase alkylation in a pressure unit at 300 psig and temperatures of 770° F. and 650° F. The reaction conditions were as follows:

| | |
|---|---|
| Ethylene feed rate, g. hr$^{-1}$ | 12 |
| Benzene feed rate, ml. hr$^{-1}$ | 382 |
| Ethylene/benzene mole ratio | 1:10 |
| WHSV ethylene | 4 |

Liquid product samples were taken at 6 and 24 on stream hours and were analyzed by GC.

The results are summarized in Table 8 below.

TABLE 8

Low Pressure Ethylbenzene Production

| Catalyst No. | Run No. | Temp., °F. | Pres., PSIG | TOS, Hrs. | Ethylene Conv., % | XYL/EB | DEB/EB | C9+/EB |
|---|---|---|---|---|---|---|---|---|
| 1. (Unbound MCM-22) | 9-1 | 770 | 300 | 6 | 98.1 | | | |
| | | | | 24 | 98.6 | | | |
| | | | | 48 | 97.7 | 0.002 | 0.047 | 0.07 |
| 1. (Unbound MCM-22) | 9-2 | 650 | 300 | 6 | 99.5 | 0.0015 | 0.089 | 0.098 |
| | 9-2 | | | 24 | 99.4 | <0.0005 | 0.088 | 0.097 |

TABLE 8-continued

| Catalyst No. | Run No. | Temp., °F. | Pres., PSIG | TOS, Hrs. | Ethylene Conv., % | XYL/EB | DEB/EB | C9+/EB |
|---|---|---|---|---|---|---|---|---|
| 2. (Al/MCM-22 Extr) | 9-3 | 770 | 300 | 6 | 96.1 | | | |
| | | | | 24 | 94.5 | 0.001 | 0.089 | 0.099 |
| 2. (Al/MCM-22 Extr) | 9-4 | 650 | 300 | 6 | 97.7 | | | |
| | | | | 24 | 97.3 | <0.0005 | 0.087 | 0.099 |
| 3. (Stmd ZSM-5 Extr) | 9-5 | 770 | 300 | 6 | 99.8 | 0.0018 | 0.072 | 0.135 |
| | | | | 24 | 99.9 | 0.00157 | 0.074 | 0.081 |
| 3. (Stmd ZSM-5 Extr) | 9-6 | 650 | 300 | 6 | 94.9 | 0.00126 | 0.181 | 0.202 |
| | | | | 24 | 94.8 | 0.0011 | 0.185 | 0.208 |
| 4. (Unstmd ZSM-5 Extr) | 9-7 | 770 | 300 | 6 | 99.7 | 0.0090 | 0.046 | 0.058 |
| | | | | 24 | 98.7 | 0.0086 | 0.047 | 0.059 |
| 4. (Unstmd ZSM-5 Extr) | 9-8 | 650 | 300 | 6 | 98.8 | 0.0022 | 0.119 | 0.146 |
| | | | | 24 | 98.7 | 0.0033 | 0.128 | 0.157 |

Note:
Benzene (B) Ethylbenzene (EB) Xylene (Xyl) Di-Ethylbenzene (DEB)

EXAMPLE 10

Catalyst No. 2 identified in Example 9 above (alumina bound extrudate of MCM-22) was tested in a high pressure, liquid phase ethylation of benzene in a pressure unit at 500 psig and 400°-500° F., using a 10:1 molar ratio of benzene to ethylene, as in Example 9 above.

The results are shown in Table 10 below.

Comparison of the results in Tables 8 and 10 shows that operation in the liquid phase is preferred because the yield of poly-ethylated products is reduced. This is illustrated by the comparison below in Table 9.

TABLE 9

| | Gas/Liquid Phase EB Synthesis | |
|---|---|---|
| Process Conditions | Gas Phase Example 9 | Liquid Phase Example 10 |
| Pressure, psig (kPa) | 300 (2170) | 500 (3550) |
| Temperature, °F. (°C.) | 650 (343) | 412 (211) |
| C2= WHSV | 4.0 | 0.3 |
| C2= conversion, wt. pct. | 97.3 | 99.6 |
| Selectivity, pct. | | |
| Xylene/EB | <0.0005 | 0.000 |
| DEB/EB | 0.087 | 0.066 |
| C9+/EB | 0.099 | 0.070 |

TABLE 10

| | | | | | Ethylbenzene Production over MCM-22 | | | | | |
|---|---|---|---|---|---|---|---|---|---|---|
| Run No | Max T, °F. | Avg T, °F. | HOS | C2= WHSV | C2= Conv, % | EB/B | Xyl/B | DEB/B | C9+/EB | B:C2= Ratio |
| 10-1 | 412 | 388 | 2 | 0.3 | 98.3 | 0.148 | 0.000 | 0.064 | 0.083 | 10:1 |
| 10-2 | 412 | 388 | 23 | 0.3 | 99.6 | 0.148 | 0.000 | 0.066 | 0.070 | 10:1 |
| 10-3 | 414 | 389 | 45 | 0.3 | 99.6 | 0.151 | 0.000 | 0.067 | 0.070 | 10:1 |
| 10-4 | 414 | 389 | 67 | 0.3 | 99.9 | 0.151 | 0.000 | 0.065 | 0.069 | 10:1 |
| 10-5 | 416 | 387 | 113 | 0.3 | 99.8 | 0.154 | 0.000 | 0.063 | 0.067 | 10:1 |
| 10-6 | 456 | 435 | 138 | 0.3 | 100 | 0.145 | 0.000 | 0.063 | 0.068 | 10:1 |
| 10-7 | 457 | 436 | 163 | 0.3 | 98.1 | 0.153 | 0.000 | 0.067 | 0.071 | 10:1 |
| 10-8 | 457 | 435 | 200 | 0.3 | 100 | 0.157 | 0.000 | 0.068 | 0.072 | 10:1 |
| 10-9 | 458 | 436 | 216 | 0.3 | 100 | 0.154 | 0.000 | 0.066 | 0.070 | 10:1 |
| 10-10 | 459 | 436 | 245 | 0.3 | 100 | 0.154 | 0.000 | 0.066 | 0.069 | 10:1 |
| 10-11 | 474 | 443 | 270 | 0.5 | 100 | 0.207 | 0.000 | 0.159 | 0.192 | 6:1 |
| 10-12 | 468 | 426 | 294 | 0.65 | 100 | 0.234 | 0.000 | 0.183 | 0.233 | 4.6:1 |

Note:
Benzene (B) Ethylbenzene (EB) Xylene (Xyl) Di-Ethylbenzene (DEB)

We claim:

1. A process for the production of ethylbenzene, said process comprising alkylating benzene with ethylene under liquid phase conditions in the presence of a solid, porous acidic alkylation catalyst comprising a crystalline material characterized by an X-ray diffraction pattern including values substantially as set out in Table 1 of the specification.

2. A process according to claim 1, wherein the synthetic porous crystalline material is characterized by an X-ray diffraction pattern including the values substantially as set forth in Table 2 of the specification.

3. A process according to claim 1, wherein the synthetic porous crystalline material is characterized by an X-ray diffraction pattern including the values substantially as set forth in Table 3 of the specification.

4. A process according to claim 1, wherein the synthetic porous crystalline material is characterized by an X-ray diffraction pattern including the values substantially as set forth in Table 4 of the specification.

5. A process according to claim 1, wherein the synthetic porous crystalline material has a composition comprising the molar relationship $$X_2O_3:(n)YO_2,$$

wherein n is at least about 10, X is a trivalent element and Y is a tetravalent element.

6. A process according to claim 2, wherein the synthetic porous crystalline material has the structure of MCM-22.

7. A process according to claim 6, wherein the MCM-22 is in the hydrogen form.

8. A process according to claim 1, wherein the catalyst comprises MCM-22 and a binder selected from alumina, silica, silica-alumina or zirconia.

9. A process according to claim 1, wherein the liquid phase alkylation is carried out at a pressure from 400 to 1000 psig and a temperature from 300° to 700° F.

10. A process according to claim 1, wherein the molar ratio of ethylene to benzene is from about 1:1 to 30:1, based on the fresh feed.

11. A process according to claim 1, wherein the molar ratio of ethylene to benzene is from about 5:1 to 20:1, based on the fresh feed.

* * * * *

UNITED STATES PATENT AND TRADEMARK OFFICE
CERTIFICATE OF CORRECTION

PATENT NO. : 5,334,795
DATED : August 2, 1994
INVENTOR(S) : Q.N. Le

It is certified that error appears in the above-indentified patent and that said Letters Patent is hereby corrected as shown below:

On the title page, item [75]: delete P. Chu and M.E. Landis as inventors.

Col. 16, Claim 6, line 35, "2" should be --1--.

On the title page, item [19] "Chu et al" should read --Le--.

Signed and Sealed this

Eighteenth Day of October, 1994

Attest:

BRUCE LEHMAN

Attesting Officer

Commissioner of Patents and Trademarks